(12) United States Patent
Xiao et al.

(10) Patent No.: US 9,981,957 B2
(45) Date of Patent: May 29, 2018

(54) SYNTHETIC PROCESS

(71) Applicant: THE UNIVERSITY OF LIVERPOOL, Liverpool (GB)

(72) Inventors: Jianliang Xiao, Liverpool (GB); Jianjun Wu, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 0 days. days.

(21) Appl. No.: 15/128,829

(22) PCT Filed: Mar. 24, 2015

(86) PCT No.: PCT/GB2015/050883
§ 371 (c)(1),
(2) Date: Sep. 23, 2016

(87) PCT Pub. No.: WO2015/145143
PCT Pub. Date: Oct. 1, 2015

(65) Prior Publication Data
US 2017/0107208 A1 Apr. 20, 2017

(30) Foreign Application Priority Data
Mar. 25, 2014 (GB) .................................. 1405359.9

(51) Int. Cl.
*C07D 409/04* (2006.01)
*C07D 211/14* (2006.01)
*C07D 211/22* (2006.01)
*C07D 211/18* (2006.01)
*C07D 211/28* (2006.01)
*C07D 211/32* (2006.01)
*C07D 211/26* (2006.01)
*C07D 405/04* (2006.01)
*C07D 211/34* (2006.01)
*C07D 401/04* (2006.01)

(52) U.S. Cl.
CPC .......... *C07D 409/04* (2013.01); *C07D 211/14* (2013.01); *C07D 211/18* (2013.01); *C07D 211/22* (2013.01); *C07D 211/26* (2013.01); *C07D 211/28* (2013.01); *C07D 211/32* (2013.01); *C07D 211/34* (2013.01); *C07D 401/04* (2013.01); *C07D 405/04* (2013.01); C07B 2200/13 (2013.01)

(58) Field of Classification Search
CPC .................................................... C07D 409/04
USPC ........................................................ 546/185
See application file for complete search history.

(56) References Cited

FOREIGN PATENT DOCUMENTS

EP 2 762 467 A1 8/2014

OTHER PUBLICATIONS

Zincke Reaction, Wikipedia, p. 1-6 (2017).*
International Search Report and Written Opinion prepared for PCT/GB2015/050883, dated May 13, 2015, 10 pages.
Zincke et al., "Ueber Dinitrophenylpyridiniumchlorid and dessen Umwandlungsproducte", Justus Liebigs Annalen Der Chemie, 341, 1905, 365-379.
Lettre et al., "Zur Darstellung von Derivaten des Nicotinsaureamids", Justus Liebigs Annalen Der Chemie, 579, 18 1953,123-132.
Ye et al., "Iridium-Catalyzed Asymmetric Hydrogenation of Pyridium Salts", Angewandte Chemie International Edition, vol. 51, 2012, 10181-10184.
Wu et al., "Efficient and Chemoselective Reduction of Pyridines to Tetrahydropyridines and Piperdines via Rhodium-Catalyzed Transfer Hydrogenation", Advanced Synthesis Catalyst, 2013, 355, 35-40.
UK Search Report prepared for application No. GB1405359.9, dated Oct. 31, 2014, 4 pages.
Zincke et al., "II. On dinitrophenylpyridinium chloride and its conversion products. On the action of aliphatic amines on dinitrophenylpyridinium chloride," Liebigs Ann. chem. 341(3), 365-379 (English translation).
Lettre et al., "On the preparation of derivatives of nicotinamide," Liebigs Ann. chem. 59(2), 123-132 (English translation ).
O'Hagan, D., "Pyrrole, pyrrolidine, pyridine, piperidine and tropane alkaloids," Nat. Prod. Rep., 2000, 17, 435-446.
Laschat, S. and Dickner, T., "Stereoselective Synthesis of Piperidines," Synthesis, 2000, 13, 1781-1783.
Weintraub, P. et al., "Recent advances in the synthesis of piperidones and piperidines," Tetrahedron, 2003, 59, 2953-2989.
Buffat, M., "Synthesis of piperidines," Tetrahedron, 2004, 60, 1701-1729.
Merino, P. et al., "Recent Advances on the Synthesis of Piperidines Through Ruthenium-Catalyzed Ring-Closing Metathesis (RCM) Reactions," Heterocycles, 2012, 84, 75-100.
Glorius, F., "Asymmetric hydrogenation of aromatic compounds," Org. Biomol. Chem., 2005, 3, 4171-4175.
Wang, D. et al., "Asymmetric Hydrogenation of Heteroarenes and Arenes," Chem. Rev., 2012, 112, 2557-2590.
Yu, Z. et al., "Brønsted Acid Activation Strategy in Transition-Metal Catalyzed Asymmetric Hydrogenation of N-Unprotected Imines, Enamines, and N-Heteroaromatic Compounds," Angew. Chem. Int. Ed., 2012, 51, 6060-6072.

* cited by examiner

*Primary Examiner* — Taofiq A Solola
(74) *Attorney, Agent, or Firm* — Barnes & Thornburg LLP

(57) ABSTRACT

The present invention relates to a process for preparing substituted piperidine compounds and especially chiral substituted piperidine compounds. The process involves reacting a substituted pyridinium ion with an amine as defined herein, in the presence of a hydrogen donor, a catalysts and a suitable solvent.

14 Claims, 1 Drawing Sheet

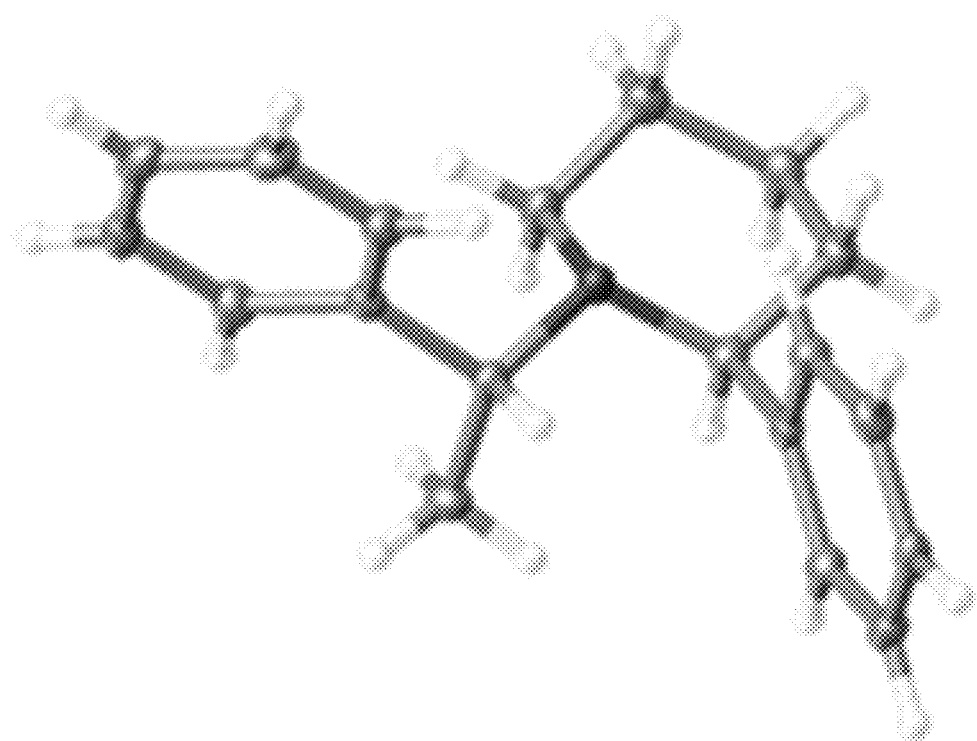

SYNTHETIC PROCESS

CROSS-REFERENCE TO RELATED APPLICATIONS

This application is a U.S. national stage entry under 35 U.S.C. § 371(b) of PCT International Application No. PCT/GB2015/050883, filed Mar. 24, 2015, and claims the benefit under 35 U.S.C. § 119 of United Kingdom Patent Application No. 1405359.9, filed Mar. 25, 2014, the entire disclosures of all are expressly incorporated by reference herein.

This invention relates to a process for synthesising substituted piperidine compounds. More particularly, but not exclusively, the present invention relates to a process for synthesising chiral substituted piperidine compounds. Substituted piperidine compounds are useful for a variety of important commercial applications, especially in the pharmaceutical, biotechnology and agrochemical fields.

BACKGROUND

Piperidine and its derivatives are ubiquitous building blocks in the synthesis of many naturally occurring products, pharmaceuticals and fine chemicals. In 2008, there were twenty one piperidine-containing drugs in Top 200 Selling Drugs, which showed sales of $11.2 billion (USD), with $2.5 billion for OxyContin (Purdue Pharma), $1.1 billion for the Concerta (Johnson & Johnson) and $0.31 billion for the Focalin XR (Novartis). In addition, Paxil (GSK), a chiral piperidine drug, had attributed total sales of $11.7 billion (USD) in 1997-2006.

Apart from the significant drug market, chiral piperidine compounds have also been studied extensively in both academic institutions and R&D sectors of pharmaceutical and biotechnology companies, due to their abundant presence as naturally occurring products which often have unique bioactivities, such as anopterine, pergoline, scopolamine and morphine, coniine, pipecoline, anabasine and anatabine, β-conhydrine, pipecolic acid, sedamine, indolizidine alkaloids and aza-sugars. As a result, the market for the chiral-piperidine based fine chemicals, which serve as building blocks for drug discovery and development, is of great significance and increasingly expanding due to the increasing demand mainly from pharmaceutical companies and generic drug producers.

While small chiral, cyclic amines such as piperidines are privileged chemical scaffolds, present in many natural products and pharmaceutical compounds[1], approaches for the effective, atom economic synthesis of such compounds from simple starting materials are rare.

One attractive approach is the catalytic reduction of the parent heterocycles using hydrogen ($H_2$) or another hydrogen source. Although much progress has been made in the asymmetric reduction of the more reactive benzofused heterocycles, direct synthesis of chiral piperidines by reduction of simple pyridine derivatives remains extremely challenging.[2]

It is the aromatic nature of pyridine (resonance energy 27 kcal/mol), coupled with the tendency of pyridines to poison metal catalysts by coordination through the basic nitrogen atom, that makes the reduction of pyridines a particularly challenging task, typically requiring heterogeneous catalysts and forcing reaction conditions. As a result, the great advances made in homogeneous asymmetric hydrogenation have not been brought to bear, and a simple cost-effective asymmetric reduction of pyridines remains unrealised.[2]

It is therefore an objective of the present application to provide a facile process for the formation of substituted piperidines.

It is a further objective to provide a facile process for the formation of chiral piperidines by the hydrogenation of pyridines.

BRIEF SUMMARY OF THE DISCLOSURE

In a first aspect, the present invention provides a process for the preparation of a substituted piperidine compound of formula I:

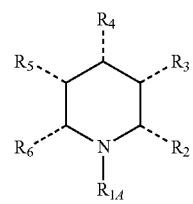

wherein:
$R_{1A}$, is a substituent group as defined herein;
$R_2$, $R_3$, $R_4$, $R_5$, and $R_6$ are each independently selected from hydrogen or a substituent group as defined herein, with the proviso that at least one of $R_2$, $R_3$, $R_4$, $R_5$, and $R_6$ is a substituent group as defined herein;
the process comprising reacting, in the presence of a suitable solvent, a pyridinium salt of the formula:

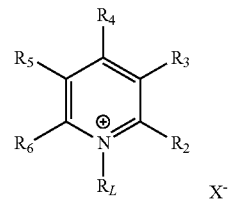

wherein:
$X^-$ is a counter ion,
$R_L$ is a substituent group as defined herein,
and $R_2$, $R_3$, $R_4$, $R_5$, and $R_6$ are as defined above;
with an amine of the formula:

wherein:
$R_{1A}$ is a substituent group as defined above;
in the presence of a hydrogen donor and a catalyst that is capable of generating hydride from the hydrogen donor.

In a particular aspect, the present invention provides a process for the preparation of a chiral substituted piperidine compound of formula I:

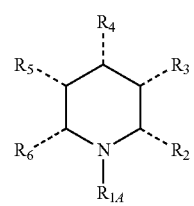

wherein:
$R_{1A}$, $R_2$, $R_3$, $R_4$, $R_5$, and $R_6$ are each as defined herein, with the proviso that at least one of $R_2$, $R_3$, $R_4$, $R_5$, and $R_6$ is a substituent group as defined herein and the carbon atom to which the group is attached is present in the (R) or (S) stereochemical configuration;

the process comprising reacting, in the presence of a suitable solvent, a pyridinium salt of the formula:

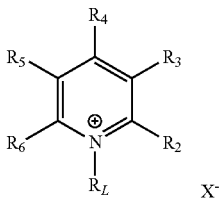

wherein:
$X^-$, $R_L$, $R_2$, $R_3$, $R_4$, $R_5$, and $R_6$ are as defined above;
with a chiral amine of the formula:

wherein:
$R_{1A}$ is a substituent group as defined above;
in the presence of a hydrogen donor and a catalyst that is capable of generating hydride from the hydrogen donor.

In a further aspect, the present invention provides a process for the preparation of a substituted piperidine compound of formula II:

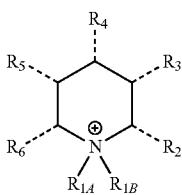

wherein:
$R_{1A}$ is a substituent group as defined herein;
$R_{1B}$ is a substituent group as defined herein;
$R_2$, $R_3$, $R_4$, $R_5$, and $R_6$ are each independently selected from hydrogen or a substituent group as defined herein, with the proviso that at least one of $R_2$, $R_3$, $R_4$, $R_5$, and $R_6$ is a substituent group as defined herein;

the process comprising reacting, in the presence of a suitable solvent, a pyridinium salt of the formula:

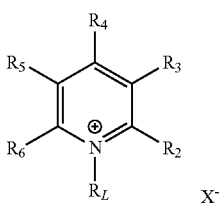

wherein:
$X^-$, $R_L$, $R_2$, $R_3$, $R_4$, $R_5$, and $R_6$ are as defined above;
with an amine of the formula:

wherein:
$R_{1A}$ and $R_{1B}$ are as defined above;
in the presence of a hydrogen donor and a catalyst capable of generating hydride from the hydrogen donor.

In a particular aspect, the present invention provides a process for the preparation of a chiral substituted piperidine compound of formula II above:

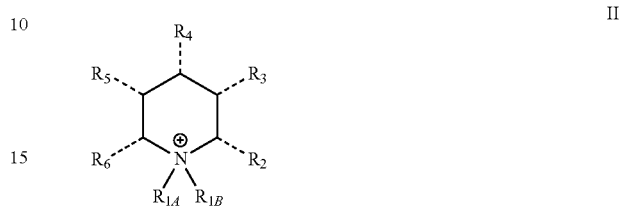

wherein:
$R_{1A}$ is a substituent group as defined herein;
$R_{1B}$ is a substituent group as defined herein;
$R_2$, $R_3$, $R_4$, $R_5$, and $R_6$ are each independently selected from hydrogen or a substituent group as defined herein, with the proviso that at least one of $R_2$, $R_3$, $R_4$, $R_5$, and $R_6$ is a substituent group as defined herein and the carbon atom to which the group is attached is present in the (R) or (S) stereochemical configuration;

the process comprising reacting, in the presence of a suitable solvent, a pyridinium salt of the formula:

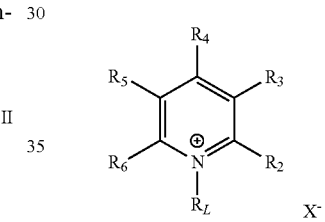

wherein:
$X^-$ is a counter ion,
$R_L$ is a substituent group as defined herein,
and $R_2$, $R_3$, $R_4$, $R_5$, and $R_6$ are as defined above;
with a chiral amine of the formula:

wherein:
$R_{1A}$ and $R_{1B}$ are as defined above;
in the presence of a hydrogen donor and a catalyst capable of generating hydride from the hydrogen donor.

In a further aspect, the present invention relates to the formation of a substituted piperidine of formula III below

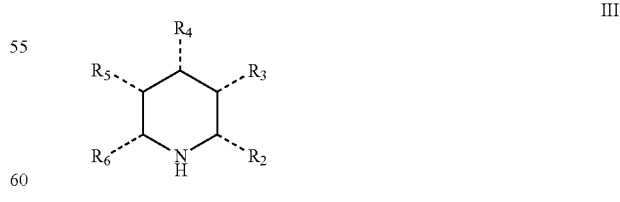

wherein:
$R_2$, $R_3$, $R_4$, $R_5$, and $R_6$ are as defined herein;
the process comprising:
forming a compound of formula I as defined above and deprotecting the compound of formula I to remove the group $R_{1A}$.

The hashed bonds are used herein in Formulae I, II and III to indicate that the carbon atom of the piperidine ring to which the R group is attached may be chiral and in either the (S) or the (R) stereochemical configuration.

In a further aspect, the present invention relates to certain novel piperidine compounds of formula I, II or III described herein (including any compounds exemplified in the example section below).

It has surprisingly been found that the processes of the present invention enable substituted piperidine compounds of formula I, II and III to be prepared by facile processes. In particular, the processes for forming compounds of formula I or II can be carried out in one pot. The resultant end products can be attained in good yields.

One particular advantage of the processes of the present invention is that the use of a chiral amine of the formula $H_2NR_{1A}$ or $HNR_{1A}R_{1B}$ enables chiral substituted piperidines of formula I, II or III to be prepared with good yields and with high enantiomeric purity. The chirality of the amine used in the reaction directly dictates the chirality of the carbon atoms to which the substituent groups $R_2$, $R_3$, $R_4$, $R_5$ and $R_6$ are attached. The ability to control the chirality of the resultant piperidine in this way (i.e. by the selection of a suitable chiral amine) and in such a facile reaction process represents a major advance in this field.

DETAILED DESCRIPTION

Definitions

Unless otherwise stated, the following terms used in the specification and claims have the following meanings set out below.

The term "hydrocarbyl" as used herein includes reference to moieties consisting exclusively of hydrogen and carbon atoms; such a moiety is an aliphatic moiety. The moiety may, for example, comprise 1, 2, 3, 4, 5, 6, 7, 8, 9, 10, 11 or 12 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); alkenyl (e.g. 2-butenyl); and alkynyl (e.g. 2-butynyl) and the like.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

The term "carbocyclyl" as used herein includes reference to a saturated (e.g. cycloalkyl) or unsaturated (e.g. aryl) ring moiety having 3, 4, 5, 6, 7, 8, 9 or 10 ring carbon atoms. In particular, carbocyclyl includes a 3- to 10-membered ring or ring system and, in particular, a 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, naphthyl, and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicycle [2.2.2]octane, bicycle[2.1.1]hexane, bicycle[1.1.1]pentane and bicyclo[2.2.1]heptyl.

The term "(1-8C)heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo [2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4] octane, 2-oxa-6-azaspiro[3.4]octane, 2-azaspiro[3.3]heptanes, 2-oxa-6-azaspiro[3.3]heptanes, 7-oxa-2-azaspiro[3.5]

nonane, 6-oxa-2-azaspiro[3.4]octane, 2-oxa-7-azaspiro[3.5] nonane and 2-oxa-6-azaspiro[3.5]nonane.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

The present invention also encompasses the formation of compounds of the invention as defined herein which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and N may be in any isotopic form, including $^{15}$N and the like.

The phrase "compound of the invention" means those compounds which are disclosed herein, both generically and specifically.

Substituted Piperidine Compounds

As stated above, the present invention provides processes for the formation of compounds of formulae I, II and III defined above.

In the compounds of formulae I, II and III above, 1, 2, 3, 4, or 5 of the groups $R_2$, $R_3$, $R_4$, $R_5$ and $R_6$ are a substituent group and the remaining groups are hydrogen.

In an embodiment, 1, 2 or 3 of the groups $R_2$, $R_3$, $R_4$, $R_5$ and $R_6$ are a substituent group and the remaining groups are hydrogen.

In a further embodiment, 1 or 2 of the groups $R_2$, $R_3$, $R_4$, $R_5$ and $R_6$ are a substituent group and the remaining groups are hydrogen.

In another embodiment, one of the groups $R_2$, $R_3$, $R_4$, $R_5$ and $R_6$ is a substituent group and the remaining groups are all hydrogen.

In yet another embodiment, $R_2$ is a substituent group and $R_3$, $R_4$, $R_5$ and $R_6$ are all hydrogen.

The $R_2$, $R_3$, $R_4$, $R_5$ and $R_6$ groups may be selected from any substituent group. The precise nature of the groups is not critical, but they are preferably carbon-linked substituent groups (i.e. the substituent group is linked to the piperidine ring via a carbon atom).

Suitable $R_2$, $R_3$, $R_4$, $R_5$ and $R_6$ substituent groups include groups containing up to 50 atoms selected from C, N, O, S and H. Examples of suitable substituent groups include (1-10C)alkyl, (2-10C)alkenyl, (2-10C)alkynyl, (3-12C)cycloalkyl, (3-12C)cycloalkyl(1-6C)alkyl, (3-12C)cycloalkenyl, (3-12C)cycloalkenyl(1-6C)alkyl, aryl, aryl(1-6C) alkyl, heteroaryl, heteroaryl(1-6C)alkyl, heterocyclyl, heterocyclyl(1-6C)alkyl, each of which is optionally further substituted by one or more groups $Q_1$. Suitably, the heteroaryl and heterocyclyl groups are carbon-linked.

In an embodiment, $R_2$, $R_3$, $R_4$, $R_5$ and $R_6$ are selected from hydrogen or a substituent group selected from (1-10C)alkyl, (2-10C)alkenyl, (2-10C)alkynyl, (3-12C)cycloalkyl, (3-12C)cycloalkyl(1-6C)alkyl, (3-12C)cycloalkenyl, (3-12C)cycloalkenyl(1-6C)alkyl, aryl, aryl(1-6C)alkyl, heteroaryl, heteroaryl(1-6C)alkyl, heterocyclyl, heterocyclyl(1-6C)alkyl, each of which is optionally further substituted by one or more groups $Q_1$ as defined herein.

In a further embodiment, $R_2$, $R_3$, $R_4$, $R_5$ and $R_6$ are selected from hydrogen or a substituent group selected from (1-10C)alkyl, (3-12C)cycloalkyl, (3-12C)cycloalkyl(1-6C)alkyl, aryl, aryl(1-6C)alkyl, heteroaryl, heteroaryl(1-6C)alkyl, heterocyclyl, heterocyclyl(1-6C)alkyl, each of which is optionally further substituted by one or more groups $Q_1$ as defined herein.

In a further embodiment, $R_2$, $R_3$, $R_4$, $R_5$ and $R_6$ are selected from hydrogen or a substituent group selected from (1-10C)alkyl, aryl, aryl(1-6C)alkyl, heteroaryl, heteroaryl(1-6C)alkyl, heterocyclyl, heterocyclyl(1-6C)alkyl, each of which is optionally further substituted by one or more groups $Q_1$ as defined herein.

Suitably, the $Q_1$ substituent groups are each independently selected from halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $Q_1$ is a group of the formula:

-$L^1$-$L^2$-$R_A$ wherein $L^1$ is absent or a linker group of the formula —[$CR_b R_c$]$_n$— in which n is an integer selected from 1, 2, 3 or 4, and $R_b$ and $R_c$ are each independently selected from hydrogen or (1-4C)alkyl;

$L^2$ is absent or is selected from O, S, SO, $SO_2$, $N(R_d)$, C(O), C(O)O, OC(O), CH(O$R_d$), C(O)N($R_d$), N($R_d$)C(O), N($R_d$)C(O)N($R_e$), S(O)$_2$N($R_d$), or N($R_d$)$SO_2$, wherein $R_d$ and $R_e$ are each independently selected from hydrogen or (1-4C)alkyl; and $R_A$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_A$ is optionally further substituted by one or more substituent groups independently selected from oxo, halo, cyano, nitro, hydroxy, $NR_fR_g$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, CON$R_fR_g$, and SO$_2$N$R_fR_g$; wherein $R_f$ and $R_g$ are each independently selected from hydrogen, (1-4C)alkyl or (3-6C)cycloalkyl or (3-6C)cycloalkyl(1-2C)alkyl; or $R_f$ and $R_g$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_hR_i$ (where $R_h$ and $R_i$ are each independently selected from hydrogen, (1-3C)alkyl, (3-6C)cycloalkyl, or (3-6C)cycloalkyl(1-2C)alkyl);

or $R_A$ is a group having the formula:

-$L^3$-$L^4$-$R_B$ wherein $L^3$ is absent or a linker group of the formula —[$CR_j R_k$]$_n$— in which n is an integer selected from 1, 2, 3 or 4, and $R_j$ and $R_k$ are each independently selected from hydrogen or (1-4C)alkyl;

$L^4$ is absent or is selected from O, S, SO, $SO_2$, $N(R_l)$, C(O), C(O)O, OC(O), CH(O$R_l$), C(O)N($R_l$), N($R_l$)C(O), N($R_l$)C(O)N($R_m$), S(O)$_2$N($R_l$), or N($R_l$)$SO_2$, wherein $R_l$ and $R_m$ are each independently selected from hydrogen or (1-4C)alkyl; and $R_B$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl.

In an embodiment, each $Q_1$ substituent group is independently selected from halo, trifluoromethyl, trifluoromethoxy, cyano, nitro, hydroxy, amino, carboxy, carbamoyl, sulphamoyl, ureido, (1-6C)alkyl, or $Q_1$ is a group of the formula:

-$L^1$-$L^2$-$R_A$ wherein $L^1$ is absent or a linker group of the formula —[$CR_b R_c$]$_n$— in which n is an integer selected from 1, 2, 3 or 4, and $R_b$ and $R_c$ are each independently selected from hydrogen or (1-4C)alkyl;

$L^2$ is absent or is selected from O, S, SO, $SO_2$, $N(R_d)$, C(O), C(O)O, OC(O), CH(O$R_d$), C(O)N($R_d$), N($R_d$)C(O), N($R_d$)C(O)N($R_e$), S(O)$_2$N($R_d$), or N($R_d$)$SO_2$, wherein $R_d$ and $R_e$ are each independently selected from hydrogen or (1-4C)alkyl; and $R_A$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_A$ is optionally further substituted by one or more substituent groups independently selected from oxo, halo, cyano, nitro, hydroxy, $NR_fR_g$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, CON$R_fR_g$, and SO$_2$N$R_fR_g$; wherein $R_f$ and $R_g$ are each independently selected from hydrogen, (1-4C)alkyl or (3-6C)cycloalkyl or (3-6C)cycloalkyl(1-2C)alkyl; or $R_f$ and $R_g$ can be linked such that, together with the nitrogen atom to which they are attached, they form a 4-6 membered heterocyclic ring.

In a further embodiment, each $Q_1$ substituent group is independently selected from halo, trifluoromethyl, trifluoromethoxy, cyano, nitro, hydroxy, amino, carboxy, carbamoyl, sulphamoyl, ureido, (1-6C)alkyl, or $Q_1$ is a group of the formula:

-$L^1$-$L^2$-$R_A$ wherein $L^1$ is absent or a linker group of the formula —[$CR_b R_c$]$_n$— in which n is an integer selected from 1, 2, 3 or 4, and $R_b$ and $R_c$ are each independently selected from hydrogen or (1-4C)alkyl;

$L^2$ is absent or is selected from O, S, SO, $SO_2$, $N(R_d)$, C(O), C(O)O, OC(O), CH(O$R_d$), C(O)N($R_d$), N($R_d$)C(O), N($R_d$)C(O)N($R_e$), S(O)$_2$N($R_d$), or N($R_d$)$SO_2$, wherein $R_d$ and $R_e$ are each independently selected from hydrogen or (1-4C)alkyl; and $R_A$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_A$ is optionally further substituted by one or more substituent groups independently selected from oxo, halo, cyano, nitro, hydroxy, $NR_fR_g$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_fR_g$, and $SO_2NR_fR_g$; wherein $R_f$ and $R_g$ are each independently selected from hydrogen, (1-4C)alkyl or (3-6C)cycloalkyl or (3-6C)cycloalkyl(1-2C)alkyl; or $R_f$ and $R_g$ can be linked such that, together with the nitrogen atom to which they are attached, they form a 4-6 membered heterocyclic ring.

The $R_{1A}$ group may be any suitable substituent group and is optionally a substituent group as defined above for $R_2$, $R_3$, $R_4$, $R_5$ and $R_6$. Suitably, $R_{1A}$ is a substituent group selected from (1-10C)alkyl, (3-12C)cycloalkyl, (3-12C)cycloalkyl(1-6C)alkyl, aryl(1-6C)alkyl, heteroaryl(1-6C)alkyl or heterocyclyl(1-6C)alkyl, each of which is optionally substituted with a group $Q_1$ as defined above. Most suitably, $R_{1A}$ is (1-10C)alkyl or aryl(1-6C)alkyl, each of which is optionally substituted with a group $Q_1$ as defined above.

In an embodiment, $R_{1A}$ is an aliphatic group, such as a (1-10C)alkyl group.

Suitably, $R_{1A}$ is a chiral group comprising a chiral carbon atom within the group.

In an embodiment, $R_{1A}$ has the formula X:

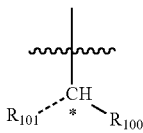

wherein ⌇⌇⌇ represents the point of attachment to the N atom of the piperidine ring and * represents a chiral carbon atom; and $R_{100}$ and $R_{101}$ are different substituent groups that, together with the carbon atom to which they are attached, form a substituent group $R_{1A}$ selected from any one of the options set out above.

Suitably, $R_{101}$ is (1-6C)alkyl, for example methyl or ethyl, and $R_{100}$ is a group selected from a (1-8C)alkyl, aryl or aryl(1-6C)alkyl, heteroaryl or heteroaryl(1-6C)alkyl each of which is optionally substituted by a group $Q_1$ as defined herein.

The $R_{1B}$ group may be any suitable substituent group and is optionally a substituent group as defined above for $R_2$, $R_3$, $R_4$, $R_5$ and $R_6$. Suitably, $R_{1B}$ is a substituent group selected from (1-10C)alkyl, (3-12C)cycloalkyl, (3-12C)cycloalkyl(1-6C)alkyl, aryl(1-6C)alkyl, heteroaryl(1-6C)alkyl or heterocyclyl(1-6C)alkyl, each of which is optionally substituted with a group $Q_1$ as defined above. Most suitably, it is (1-10C)alkyl or aryl(1-6C)alkyl, each of which is optionally substituted with a group $Q_1$ as defined above.

In a particular embodiment, $R_{1B}$ is (1-10C)alkyl.

In an embodiment, the compounds of formula I have the structural formula IA shown below (i.e. $R_6$ is H):

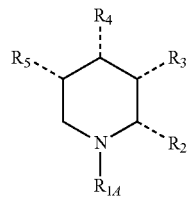

wherein:

$R_{1A}$, $R_2$, $R_3$, $R_4$ and $R_5$ each have any one of the definitions set out herein.

In an embodiment, the compounds of formula I have the structural formula IB shown below (i.e. $R_4$ and $R_6$ are H):

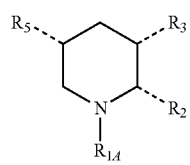

wherein:

$R_{1A}$, $R_2$, $R_3$ and $R_5$ each have any one of the definitions set out herein.

In an embodiment, the compounds of formula I have the structural formula IC shown below (i.e. $R_3$, $R_4$, $R_5$ and $R_6$ are H):

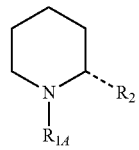

wherein:

$R_{1A}$, and $R_2$ each have any one of the definitions set out herein.

In an embodiment, the compounds of formula II have the structural formula IIA shown below (i.e. $R_6$ is H):

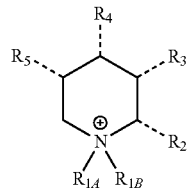

wherein:

$R_{1A}$, $R_{1B}$, $R_2$, $R_3$, $R_4$ and $R_5$ each have any one of the definitions set out herein.

In an embodiment, the compounds of formula II have the structural formula IIB shown below (i.e. $R_4$ and $R_6$ are H):

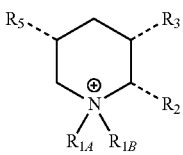

IIB wherein:

$R_{1A}$, $R_{1B}$, $R_2$, $R_3$ and $R_5$ each have any one of the definitions set out herein.

In an embodiment, the compounds of formula I have the structural formula IIC shown below (i.e. $R_3$, $R_4$, $R_5$ and $R_6$ are H):

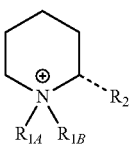

IIC wherein:

$R_{1A}$, $R_{1B}$ and $R_2$ each have any one of the definitions set out herein.

In an embodiment, the compounds of formula III have the structural formula IIIA shown below (i.e. $R_6$ is H):

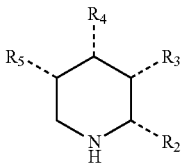

IIIA wherein:

$R_2$, $R_3$, $R_4$ and $R_5$ each have any one of the definitions set out herein.

In an embodiment, the compounds of formula III have the structural formula IIIB shown below (i.e. $R_4$ and $R_6$ are H):

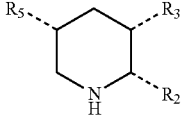

IIIB wherein:

$R_2$, $R_3$ and $R_5$ each have any one of the definitions set out herein.

In an embodiment, the compounds of formula III have the structural formula IIIC shown below (i.e. $R_3$, $R_4$, $R_5$ and $R_6$ are H):

IIIC wherein:

$R_2$ has any one of the definitions set out herein.

Particular examples of compounds of the formula I are provided in the accompanying examples.

The Pyridinium Salt

In the pyridinium salt used as the starting material in the process of the present invention, $R_2$, $R_3$, $R_4$, $R_5$ and $R_6$ each have any one of the definitions set out above in relation to the compounds of formulae I, II or III.

Suitably $R_L$ is any substituent group that can be bound the pyridine nitrogen to form a pyridinium salt or hydrogen formed in situ by protonation with an acid. Exemplary $R_L$ groups include (1-10C)alkyl, (2-10C)alkenyl, (2-10C)alkynyl, (3-12C)cycloalkyl, (3-12C)cycloalkyl(1-6C)alkyl, (3-12C)cycloalkenyl(1-6C)alkyl, aryl(1-6C)alkyl, heteroaryl(1-6C)alkyl, or heterocyclyl(1-6C)alkyl, each of which is optionally further substituted by one or more groups $Q_1$ as defined hereinbefore. Suitably, the heteroaryl and heterocyclyl groups are carbon-linked.

In an embodiment, $R_L$ is selected from (1-10C)alkyl, (2-10C)alkenyl, (2-10C)alkynyl, (3-12C)cycloalkyl(1-6C)alkyl, or aryl(1-6C)alkyl, each of which is optionally further substituted by one or more groups $Q_1$ as defined herein.

In a particular embodiment, $R_L$ is (1-10C)alkyl, e.g. ethyl.

The counter ion, $X^-$, may be any suitable counter ion. In an embodiment, $X^-$ is a halide. Suitably, $X^-$ is bromo or iodo. Most suitably, $X^-$ is iodo.

The Amine

The amine used in the processes of the present invention may be any primary amine ($H_2NR_{1A}$) or any secondary amine ($HNR_{1A}R_{1B}$).

Suitably, the amine is any primary amine (i.e. $H_2NR_{1A}$).

The amine may be chiral, i.e. $R_{1A}$ or $R_{1B}$ comprise one or more chiral carbon atoms.

Suitably, $R_{1A}$ comprises one or more chiral atoms. Most suitably, the carbon atom directly attached to the N atom of the amine is chiral.

In an embodiment, $R_{1A}$ has the structural formula X defined above. This means that the amine may have one of the structural formulae shown below:

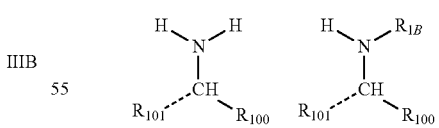

wherein $R_{1B}$, $R_{100}$ and $R_{101}$ are each as defined hereinbefore.

The amount of amine will depend on the amount of pyridinium ion present. The amine may be present in amounts of 1 molar equivalent or higher. For example, there may be between 1 and 20 molar equivalents of amine relative to the pyridinium ion. Suitably, between 1 and 10 molar equivalents of the amine are used. Any unused/excess amine may be optionally recycled and used again in the process.

The Hydrogen Donor

Any suitable hydrogen donor may be used in the process of the present invention.

Examples of suitable hydrogen donors include hydrogen gas ($H_2$) or hydrogen donors used for transfer hydrogenation processes, such as, for example, formic acid or isopropanol.

In an embodiment, the hydrogen donor is hydrogen gas.

In another embodiment, the hydrogen donor is formic acid or isopropanol.

In a particular embodiment, the hydrogen donor is formic acid.

The amount of hydrogen donor present relative to the amine may be within the range 1:1 to 10:1 (molar equivalents of hydrogen donor to amine).

Suitably, the ratio of hydrogen donor to amine is between 1:1 to 3:1, and more suitably it is between 2:1 and 2.6:1 (molar equivalents of hydrogen donor to amine).

The Solvent

Any suitable solvent may be used for the present reaction.

Suitably, the solvent comprises water as a co-solvent. Suitably, the solvent comprises between 1 and 50% by volume of water. More suitably, the solvent comprises between 3 and 15% by volume of water. Most suitably, the solvent comprises between 4 and 8% by volume of water. Even more suitably, the solvent comprises between 6 and 7% by volume of water.

Examples of suitable solvents include dichloromethane (DCM), dichloroethane (DCE), chloroform, ethanol, tetrahydrofuran (THF), ethyl acetate and dimethylformamide (DMF).

The Catalyst

Any catalyst that is capable of forming hydride from the hydrogen donor may be used in the process of the present invention. A person skilled in the art will understand how to select suitable catalysts capable of performing this function for the particular hydrogen donor that is used.

Transition metal catalysts are suitable candidates, especially catalysts based on rhodium (Rh), iridium (Ir) and ruthenium (Ru). Catalysts comprising Cp* (pentamethylcyclopentadienyl) or cymene and halides coordinated on the transition metal atom are generally preferred.

Examples of suitable catalysts include those of the formula:

[ArMX$_2$]$_2$ where Ar is pentamethylcyclopentadienyl, benzene or cymene; M is a transition metal (e.g. Rh, Ir and Ru); and X is a halide, such as chloro, bromo or iodo In an embodiment, Ar is pentamethylcyclopentadienyl or cymene. In a further embodiment, Ar is pentamethylcyclopentadienyl.

Suitably, M is Rh.

Suitable X is chloro or iodo.

Particular examples of suitable catalysts include [Cp*RhCl$_2$]$_2$, [Cp*IrCl$_2$]$_2$ and [Cp*RhI$_2$]$_2$.

The catalyst may be present in an amount of 0.1 to 5 mol. %. Suitably, the catalyst is present in an amount of 0.2 to 2 mol. %. More suitably, the catalyst is present in an amount of 0.5 to 1.5 mol. %, e.g. at about 1 mol. %.

Reaction Conditions

The reaction is performed by mixing the pyridinium salt, the amine, the hydrogen donor and the catalyst in a suitable vessel in the presence of the solvent. The components may be added in any particular order or all at the same time. It may be necessary to control the temperature as the components are mixed.

In an embodiment, the amine and the hydrogen donor are mixed together first and then the pyridinium salt and catalysts are added to the reaction mixture.

In a further embodiment, the pyridinium salt is placed in a vessel and the amine is then added followed by the hydrogen donor (e.g. formic acid), and the catalyst (e.g. [Cp*RhCl$_2$]$_2$). The solvent is then added followed by the co-solvent (water). The temperature may be controlled by cooling the vessel during the addition of the hydrogen donor.

The reaction suitably proceeds at an elevated temperature for a period of time. A person skilled in the art will appreciate that the temperature and reaction time may be varied. Suitably, the reaction proceeds at a temperature of 25-100° C., optionally over a period of 2 to 48 hours. More suitably, the reaction proceeds at a temperature of 30-50° C., optionally over a time period of 15-24 hours. Even more suitably, the reaction proceeds at a temperature of 35-45° C. (e.g. around 40° C.), optionally over a time period of 15-24 hours.

The reaction vessel may be pressurised if hydrogen gas is used as the hydrogen donor.

If another hydrogen donor is used (such as those used for transfer hydrogenation reactions), then no pressurisation will be necessary.

As indicated above, the present invention also relates to the formation of a substituted piperidine of formula III below

III

[Structure of formula III: piperidine ring with substituents $R_2$, $R_3$, $R_4$, $R_5$, $R_6$ and NH]

wherein:

$R_2$, $R_3$, $R_4$, $R_5$, and $R_6$ are as defined herein;

the process comprising:

forming a compound of formula I as defined herein and reacting the compound of formula I to remove the group $R_{1A}$.]

A person skilled in the art will understand how to remove the group $R_{1A}$ from the piperidine compound of formula I using standard techniques. For example, the group $R_{1A}$ may be removed by using a catalytic amount of Pd/C under 1-30 atm hydrogen pressure in ethanol (with or without aqueous HCl).

The compound of formula III may then be protected in the 1-position by the addition of a suitable protecting group, such as BOC, benzyl, FMOC etc. In a particular embodiment, the protecting group BOC may be added in situ during the deprotection process.

Reaction Mechanism

Without wishing to be bound by any particular theory, it is believed that the reaction between the pyridinium ion and the amine proceeds by the following mechanism:

[Mechanism showing three structures a, b, c: pyridinium salt a converts via $H_2O$ to hemiaminal b which equilibrates to open-chain aminoaldehyde c]

a     b     c

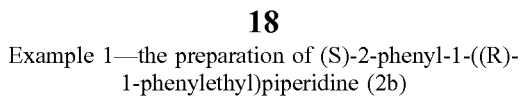

-continued

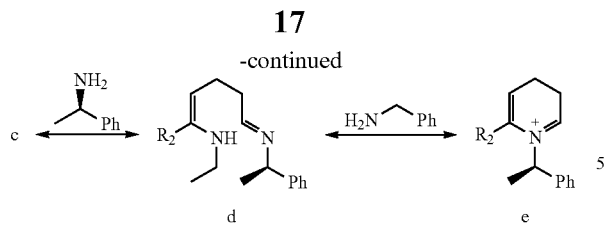

Applications

As indicated above, the process of the present invention makes substituted piperidines, and in particular chiral substituted piperidines readily accessible.

Substituted piperidines have a wide range of uses, especially in the pharmaceutical, biotechnology, agrochemical and fine chemical supply fields. As such, it is envisaged that the process of the present invention will find broad ranging applications in the pharmaceutical, agrochemical, biotech and fine chemical supply industries.

Particular examples of piperidine compounds that could be prepared by the process of the present invention include: (S) or (R)-1-N-Boc-2-methylpiperidine, (S)-1-N-Boc-2-(hydroxymethyl)piperidine, (S) or (R)-1-N-Boc-2-(hydroxymethyl)piperidine (S) or (R)-2-phenylpiperidine, (S) or (R)1-N-Boc-2-phenylpiperidine, (S) or (R)-2-(3,4-dimethylphenyl)piperidine, (S) or (R)-tert-butyl (piperidin-2-ylmethyl)carbamate, (S) or (R)-benzyl (piperidin-2-ylmethyl)carbamate hydrochloride, (S) or (R)-Coniine HCl,

EXAMPLES

The present invention is further defined with reference to the accompanying figure, where:

The Figure shows the crystallographic data for compound 2b, in which $C_{19}H_{23}N$, M=265.38, orthorhombic, space group $P2_12_12_1$ (no. 19), a=7.8158 (6) Å, b=10.3447 (7) Å, c=18.8075 (14) Å, V=1520.63 (19) Ø$^3$, Z=4, T=100.0 K, μ(Mo kα)=0.499 mm−1, Dcalc=1.159 g/mm$^3$, 13955 reflections measured (9.4≤2Θ≤149.24), 3073 unique (Rint=0.0281) which were used in all calculations. The final R1 was 0.0305 (>2sigma(I)) and wR2 was 0.0776 (all data).

Materials

Unless otherwise specified, the chemicals were obtained commercially from Aldrich, Alfa Aesar, Apollo Scientific or TCI and used without further purification. Silica gel plates (GF$_{254}$) were used for TLC monitoring and silica gel (230-400 mesh) was used for running column chromatography. NMR spectra were recorded on a Bruker 400 MHz NMR spectrometer with TMS as the internal standard. The mass spectra were obtained by chemical ionization (CI) or electrospray ionization (ESI).

Example 1—the preparation of (S)-2-phenyl-1-((R)-1-phenylethyl)piperidine (2b)

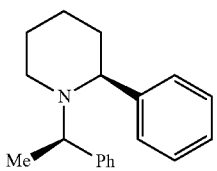

To a carousel reaction tube containing a magnetic stirring bar and (R)-(+)-α-methylbenzylamine (615 mg, 5 mmol) was added formic acid (564 mg, 12 mmol) dropwise at room temperature. After stirring the amine/acid mixture for 10 min, a pyridinium salt, N-ethyl-2-phenylpyridinium iodide (157 mg, 0.5 mmol), [Cp*RhCl$_2$]$_2$ (3.1 mg, 5 μmol), 3.75 mL of CH$_2$Cl$_2$ and 0.25 mL of distilled H$_2$O were introduced into the mixture. The reaction system was placed in a carousel reactor. The mixture was stirred at 40° C. for 22 h, cooled to room temperature and then basified with an aqueous solution of KOH. The resulting mixture was extracted with ethyl acetate (3×10 mL) and dried over Na$_2$SO$_4$. The solvent was removed under reduced pressure, and the residue was purified by column chromatography (EtOAc/hexane) to give the desired product 2b in 86% yield.

Analytic Data:

$^1$H NMR (CDCl$_3$, 400 MHz) δ (ppm): 7.49-7.42 (m, 4H), 7.35-7.18 (m, 6H), 3.83 (q, J=6.8 Hz, 1H), 3.50 (dd, J=10.0, 2.8 Hz, 1H), 2.56 (dt, J=11.6, 2.6 Hz, 1H), 2.22 (td, J=11.0, 3.0 Hz, 1H), 1.80-1.26 (m, 6H), 1.18 (d, J=6.8 Hz, 3H); $^{13}$C NMR (CDCl$_3$, 100 MHz) δ (ppm): 145.4, 144.9, 128.6, 127.9, 126.68, 127.65, 127.0, 126.2, 65.7, 55.1, 45.2, 37.3, 26.4, 25.8, 8.2; HRMS for $C_{19}H_{24}N$ [M+H]$^+$: m/z calcd 266.1903, found 266.1906.

Crystallographic data for compound 2b is shown in the Figure.

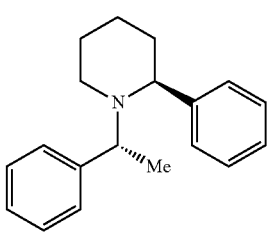

Examples 2-23

Using the procedure outlined in Example 1 above and the appropriate amine, the following compounds were prepared:

TABLE 1

Transamination of 2-substituted pyridiniums to piperidines.[a]

| Example | Substrate | Product | Yield [%][b] |
|---|---|---|---|
| 1 | 1b | 2b | 86 |
| 2 | 1b | 2b' | 83[c] |
| 3 | 1c | 2c | 82 |
| 4 | 1d | 2d | 80 |
| 5 | 1e | 2e | 58 |

TABLE 1-continued

Transamination of 2-substituted pyridiniums to piperidines.[a]

| Example | Substrate | Product | Yield [%][b] |
|---|---|---|---|
| 6 | 1f | 2f | 87 |
| 7 | 1g | 2g | 33 |
| 8 | 1h | 2h | 43 |
| 9 | 1i | 2i | 86 |
| 10 | 1j | 2j | 70[c],[d] |

TABLE 1-continued

Transamination of 2-substituted pyridiniums to piperidines.[a]

[Reaction scheme: Substrate 1 (2-substituted N-ethylpyridinium iodide with R3 at 3-position and R2 at 2-position) → Product 2 (piperidine with R3 (S), R2 (R), N-substituted with (R)-CH(Me)(Ph)) using 1 mol % [Cp*RhCl2]2, 24 eq. HCOOH, 10 eq. (R)-PEA, CH2Cl2/H2O]

| Example | Substrate | Product | Yield [%][b] |
|---|---|---|---|
| 11 | 1k (N-ethyl-2-(2-naphthyl)pyridinium iodide) | 2k ((S)-2-(2-naphthyl)piperidine, N-(R)-CH(Me)(Ph)) | 85 |
| 12 | 1l (N-ethyl-2-(2-pyridyl)pyridinium iodide) | 2l ((R)-2-(2-pyridyl)piperidine, N-(S)-CH(Me)(Ph)) | 54[c] |
| 13 | 1m (N-ethyl-2-(2-furyl)pyridinium iodide) | 2m ((S)-2-(2-furyl)piperidine, N-(R)-CH(Me)(Ph)) | 71 |
| 14 | 1n (N-ethyl-2-(2-thienyl)pyridinium iodide) | 2n ((S)-2-(2-thienyl)piperidine, N-(R)-CH(Me)(Ph)) | 48 |
| 15 | 1o (N-ethyl-2-methylpyridinium iodide) | 2o ((R)-2-methylpiperidine, N-(R)-CH(Me)(Ph)) | 88 |
| 16 | 1p (N-ethyl-2-ethylpyridinium iodide) | 2p ((R)-2-ethylpiperidine, N-(R)-CH(Me)(Ph)) | 84 |

TABLE 1-continued

Transamination of 2-substituted pyridiniums to piperidines.[a]

| Example | Substrate | Product | Yield [%][b] |
|---|---|---|---|
| 17 | 1q | 2q | 82 |
| 18 | 1r | 2r | 55 |
| 19 | 1s | 2s | 82 |
| 20 | 1t | 2t | 68 |
| 21 | 1u | 2u | 83 |

TABLE 1-continued

Transamination of 2-substituted pyridiniums to piperidines.[a]

| Example | Substrate | Product | Yield [%][b] |
|---|---|---|---|
| 22[e] | 1v | 2v | 75 |
| 23 | 1w | 2w | 56 |
| 24 | | 2x | 38 |

[a]All reactions were carried out under the standard conditions: 1 (0.5 mmol), [Cp*RhCl₂]₂ (5 μmol), HCOOH (12 mmol), (R)-PEA (5 mmol), [Cp*RhCl₂]₂ (5 μmol), CH₂Cl₂/H₂O (3.75/0.25 mL), 40° C., 22 h, in air.
[b]Isolated yields.
[c](S)-PEA was used.
[d]The reaction was carried out in 2.5 mmol scale.
[e]Reaction conditions were the same as standard conditions except for using HCOOH (24 mmol), (R)-PEA (10 mmol), [Cp*RhCl₂]₂ (10 μmol), CH₂Cl₂/H₂O (7.5/0.5 mL).

Notably the isolated yields approached 90% in some cases, which would be the maximum theoretical yield of the desired product if the transamination reaction had reached equilibrium, assuming a 10:1 ration of starting material and PEA.

Analytical Data of Sample Products:

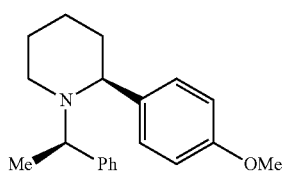

2c (S)-1-((R)-1-Phenylethyl)-2-(4-(trifluoromethyl)phenyl)piperidine (2c, unknown compound)

$^1$H NMR (CDCl$_3$, 400 MHz) δ (ppm): 7.43 (d, J=7.6 Hz, 2H), 7.38 (d, J=8.0 Hz, 2H), 7.27 (d, J=7.6 Hz, 2H), 7.17 (d, J=7.4 Hz, 2H), 6.86 (d, J=8.8 Hz, 2H), 3.83 (q, J=6.8 Hz, 1H), 3.76 (s, 3H), 3.45 (dd, J=10.8, 2.8 Hz, 1H), 2.55 (d, J=11.6 Hz, 1H), 2.20 (td, J=11.4, 2.6 Hz, 1H), 1.78-1.26 (m, 6H), 1.17 (d, J=6.8 Hz, 3H); $^{13}$C NMR (CDCl$_3$, 100 MHz) δ (ppm): 158.6, 145.0, 137.5, 128.6, 127.9, 127.6, 126.1, 114.0, 65.0, 55.4, 54.9, 45.3, 37.4, 26.6, 25.8, 8.2; HRMS for C$_{20}$H$_{26}$NO [M+H]$^+$: m/z calcd 296.2009, found 296.2005.

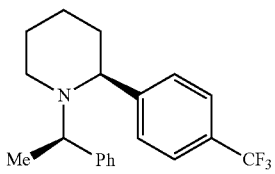

(S)-1-((R)-1-phenylethyl)-2-(4-(trifluoromethyl)phenyl)piperidine (2d, unknown compound)

$^1$H NMR (CDCl$_3$, 400 MHz) δ (ppm): 7.58 (s, 4H), 7.43 (d, J=7.8 Hz, 2H), 7.29 (t, J=7.0 Hz, 2H), 7.20 (d, J=8.0 Hz, 1H), 3.75 (q, J=6.8 Hz, 1H), 3.58 (dd, J=10.3, 2.8 Hz, 1H), 2.58 (dt, J=12.0, 2.8 Hz, 1H), 2.23 (td, J=11.0, 2.8 Hz, 1H), 1.81-1.31 (m, 6H), 1.19 (d, J=7.0 Hz, 3H); $^{13}$C NMR (CDCl$_3$, 100 MHz) δ (ppm): 149.6, 144.3, 128.0, 127.9, 127.5, 126.4, 125.7 (q, J$_{CF}$=3.7 Hz), 122.2, 65.3, 55.4, 45.1, 37.3, 26.2, 25.5, 8.3; HRMS for C$_{20}$H$_{23}$NF$_3$[M+H]$^+$: m/z calcd 334.1778, found 334.1779.

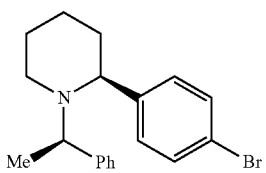

(S)-2-(4-Bromophenyl)-1-((R)-1-phenylethyl)piperidine (2i, unknown compound)

$^1$H NMR (CDCl$_3$, 400 MHz) δ (ppm): 7.46-7.34 (m, 6H), 7.29 (t, J=7.4 Hz, 2H), 7.19 (d, J=7.2 Hz, 2H), 3.78 (q, J=6.8 Hz, 1H), 3.48 (dd, J=10.8, 2.6 Hz, 1H), 2.55 (d, J=11.6 Hz, 1H), 2.21 (td, J=11.6, 2.4 Hz, 1H), 1.79-1.72 (m, 2H), 1.66-1.28 (m, 4H), 1.18 (d, J=7.2 Hz, 3H); $^{13}$C NMR (CDCl$_3$, 100 MHz) δ (ppm): 144.47, 144.46, 131.8, 129.4, 128.0, 127.6, 126.3, 120.5, 65.0, 55.1, 45.1, 37.3, 26.3, 25.6, 8.3; HRMS for C$_{19}$H$_{23}$BrN [M+H]$^+$: m/z calcd 346.0988, 344.1009, found 346.0987, 344.0995.

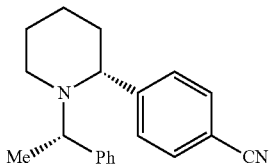

4-((R)-1-((S)-1-Phenylethyl)piperidin-2-yl)benzonitrile (2j, unknown compound)

$^1$H NMR (CDCl$_3$, 400 MHz) δ (ppm): 7.65-7.57 (m, 4H), 7.41 (d, J=12.8 Hz, 2H), 7.34-7.18 (m, 3H), 3.71 (q, J=10.8 Hz, 1H), 3.59 (dd, J=16.8, 4.8 Hz, 1H), 2.58 (d, J=19.0 Hz, 1H), 2.23 (td, J=18.0, 4.6 Hz, 1H), 1.83-1.72 (m, 4H), 1.67-1.28 (m, 4H), 1.20 (d, J=10.8 Hz, 3H); $^{13}$C NMR (CDCl$_3$, 100 MHz) δ (ppm): 151.2, 144.0, 132.6, 128.3, 128.1, 127.4, 126.5, 119.1, 110.8, 65.3, 55.6, 44.9, 37.2, 26.1, 25.4, 8.5; HRMS for C$_{20}$H$_{23}$N$_2$[M+H]$^+$: m/z calcd 291.1856, found 291.1854.

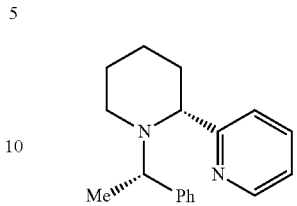

2-((R)-1-((S)-1-phenylethyl)piperidin-2-yl)pyridine (2l, unknown compound)

$^1$H NMR (CDCl$_3$, 400 MHz) δ (ppm): 8.53 (d, J=4.8 Hz, 1H), 7.67-7.61 (m, 2H), 7.46 (d, J=8.0 Hz, 2H), 7.30 (d, J=7.6 Hz, 2H), 7.19 (t, J=7.4 Hz, 1H), 7.13 (ddd, J=7.2, 5.0, 1.8 Hz, 1H), 3.78 (dd, J=10.8, 2.8 Hz, 1H), 3.72 (q, J=6.8 Hz, 1H), 2.59 (d, J=11.2 Hz, 1H), 2.28 (td, J=11.2, 2.8 Hz, 1H), 1.91-1.86 (m, 1H), 1.81-1.77 (m, 1H), 1.70-1.33 (m, 4H), 1.26 (d, J=6.8 Hz, 3H); $^{13}$C NMR (CDCl$_3$, 100 MHz) δ (ppm): 164.9, 149.0, 144.5, 136.7, 128.0, 127.6, 126.3, 122.0, 121.9, 67.2, 56.0, 44.9, 35.8, 26.2, 25.2, 8.8; HRMS for C$_{18}$H$_{23}$N$_2$ [M+H]$^+$: m/z calcd 267.1856, found 267.1863.

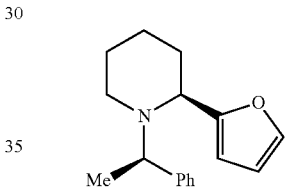

(S)-2-(Furan-2-yl)-1-((R)-1-phenylethyl)piperidine (2m, unknown compound)

$^1$H NMR (CDCl$_3$, 400 MHz) δ (ppm): 7.39 (t, J=7.6 Hz, 3H), 7.27 (d, J=7.6 Hz, 2H), 7.18 (t, J=7.2 Hz, 1H), 6.31 (dd, J=3.0, 1.8 Hz, 1H), 6.25 (d, J=3.2 Hz, 1H), 3.79 (dd, J=9.2, 3.2 Hz, 1H), 3.66 (q, J=6.8 Hz, 1H), 2.52 (dt, J=11.2, 4.0 Hz, 1H), 2.55 (td, J=10.4, 2.8 Hz, 1H), 1.97-1.72 (m, 3H), 1.54-1.30 (m, 3H), 1.26 (d, J=6.8 Hz, 3H); $^{13}$C NMR (CDCl$_3$, 100 MHz) δ (ppm): 157.2, 145.0, 141.3, 128.0, 127.8, 126.3, 110.0, 106.8, 57.3, 57.1, 45.4, 32.7, 26.0, 24.3, 11.2; HRMS for C$_{17}$H$_{22}$NO [M+H]$^+$: m/z calcd 256.1696, found 256.1689.

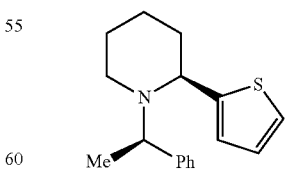

(S)-1-((R)-1-phenylethyl)-2-(thiophen-2-yl)piperidine (2n, unknown compound)

$^1$H NMR (CDCl$_3$, 400 MHz) δ (ppm): 7.42 (t, J=4.8 Hz, 3H), 7.48-7.15 (m, 6H), 6.93-6.83 (m, 2H), 3.92-3.75 (m, 2H), 2.62 (dt, J=7.0, 2.5 Hz, 1H), 2.18 (td, J=6.5, 1.8 Hz, 1H), 1.88-1.27 (m, 6H), 1.20 (d, J=4.4 Hz, 3H); $^{13}$C NMR (CDCl$_3$, 100 MHz) δ (ppm): 149.5, 144.7, 127.9, 127.7, 126.3, 126.0, 124.4, 60.1, 55.4, 45.1, 37.9, 26.0, 25.3, 9.0; HRMS for C$_{17}$H$_{22}$NS [M+H]$^+$: m/z calcd 272.1467, found 272.1463.

J=6.4 Hz, 3H); $^{13}$C NMR (CDCl$_3$, 100 MHz) δ (ppm): 146.7, 141.0, 129.4, 128.4, 128.3, 127.5, 126.6, 125.8, 58.9, 57.0, 45.2, 32.8, 28.3, 25.9, 21.3, 17.8; HRMS for C$_{20}$H$_{26}$N [M+H]$^+$: m/z calcd 280.2060, found 280.2062.

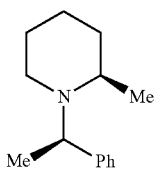

(R)-2-Methyl-1-((R)-1-phenylethyl)piperidine (2o)

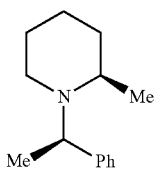

tert-butyl (((S)-1-((R)-1-Phenylethyl)piperidin-2-yl)methyl)carbamate (2s, unknown compound)

$^1$H NMR (CDCl$_3$, 400 MHz) δ (ppm): 7.42 (d, J=7.2 Hz, 2H), 7.29 (t, J=7.2 Hz, 2H), 7.19 (t, J=7.6 Hz, 1H), 4.04 (q, J=6.8 Hz, 1H), 2.84-2.77 (m, 1H), 2.36-2.31 (m, 1H), 2.15-2.09 (m, 1H), 1.72-1.56 (m, 2H), 1.43-1.28 (m, 4H), 1.25 (d, J=6.8 Hz, 3H), 1.12 (d, J=6.4 Hz, 3H); $^{13}$C NMR (CDCl$_3$, 100 MHz) δ (ppm): 145.9, 128.0, 127.8, 126.3, 56.7, 52.1, 45.0, 34.8, 26.5, 23.5, 17.2, 12.6; HRMS for C$_{14}$H$_{22}$N [M+H]$^+$: m/z calcd 204.1747, found 204.1747.

$^1$H NMR (CDCl$_3$, 400 MHz) δ (ppm): 7.38 (d, J=7.2 Hz, 2H), 7.31 (t, J=7.4 Hz, 2H), 7.22 (t, J=7.2 Hz, 1H), 4.98 (s, 1H), 4.12 (q, J=6.8 Hz, 1H), 3.40-3.35 (m, 1H), 3.29-3.23 (m, 1H), 2.72 (brs, 1H), 2.54-2.49 (m, 1H), 2.34 (ddd, J=12.0, 8.8, 2.8 Hz, 1H), 1.71-1.64 (m, 3H), 1.44 (s, 10H), 1.38-1.25 (m, 5H); $^{13}$C NMR (CDCl$_3$, 100 MHz) δ (ppm): 156.5, 145.1, 128.3, 127.6, 126.7, 79.1, 56.0, 55.2, 44.1, 41.1, 28.6, 28.2, 24.7, 23.3, 13.4; HRMS for C$_{19}$H$_{31}$N$_2$O$_2$ [M+H]$^+$: m/z calcd 319.2380, found 319.2396.

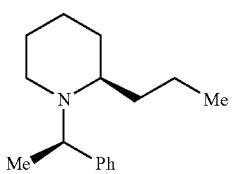

(R)-1-((R)-1-Phenylethyl)-2-propylpiperidine (2q)

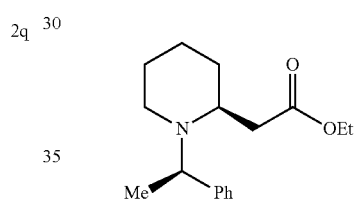

Ethyl 2-((S)-1-((R)-1-phenylethyl)piperidin-2-yl)acetate (2t)

$^1$H NMR (CDCl$_3$, 400 MHz) δ (ppm): 7.41 (d, J=7.6 Hz, 2H), 7.28 (t, J=7.6 Hz, 2H), 7.19 (t, J=7.4 Hz, 1H), 4.01 (q, J=6.6 Hz, 1H), 2.72 (brs, 1H), 2.36 (ddd, J=11.2, 8.0, 3.2 Hz, 1H), 2.23-2.18 (m, 1H), 1.69-1.28 (m, 10H), 1.25 (d, J=6.4 Hz, 3H), 0.92 (t, J=7.2 Hz, 3H); $^{13}$C NMR (CDCl$_3$, 100 MHz) δ (ppm): 146.4, 128.1, 127.6, 126.3, 56.9, 55.8, 45.2, 31.1, 29.7, 25.9, 22.8, 19.0, 14.9, 14.7; HRMS for C$_{16}$H$_{26}$N [M+H]$^+$: m/z calcd 232.2060, found 232.2057.

$^1$H NMR (CDCl$_3$, 400 MHz) δ (ppm): 7.35-7.21 (m, 5H), 4.18 (q, J=7.2 Hz, 2H), 3.86 (q, J=6.4 Hz, 1H), 2.84-2.80 (m, 1H), 2.76-2.73 (m, 1H), 1.90-1.83 (m, 1H), 1.68-1.43 (m, 6H), 1.32-1.26 (m, 8H); $^{13}$C NMR (CDCl$_3$, 100 MHz) δ (ppm): 174.7, 146.6, 128.5, 126.9, 126.8, 60.1, 55.1, 53.5, 44.6, 30.0, 25.7, 24.8, 23.4, 23.0, 14.5; HRMS for C$_{17}$H$_{26}$NO$_2$ [M+H]$^+$: m/z calcd 276.1958, found 276.1965.

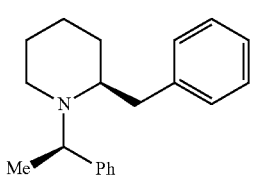

(S)-2-Benzyl-1-((R)-1-phenylethyl)piperidine (2r, unknown compound)

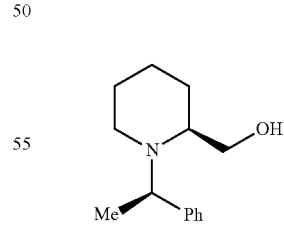

((S)-1-((R)-1-Phenylethyl)piperidin-2-yl)methanol (2u)

$^1$H NMR (CDCl$_3$, 400 MHz) δ (ppm): 7.40 (d, J=7.2 Hz, 2H), 7.32-7.17 (m, 8H), 4.02 (q, J=6.8 Hz, 1H), 3.19-3.14 (m, 1H), 3.01 (dd, J=13.2, 3.6 Hz, 1H), 2.75 (dd, J=13.0, 10.6 Hz, 1H), 2.46-2.32 (m, 2H), 1.64-1.40 (m, 6H), 1.37 (d, $^1$H NMR (CDCl$_3$, 400 MHz) δ (ppm): 7.38-7.19 (m, 5H), 4.25 (q, J=6.8 Hz, 1H), 3.62 (d, J=6.8 Hz, 2H), 2.78-2.68 (m, 1H), 2.66-2.54 (m, 2H), 1.79-1.40 (m, 5H), 1.35 (d, J=5.5 Hz, 3H), 1.31-1.19 (m, 1H); $^{13}$C NMR (CDCl$_3$, 100 MHz)

δ (ppm): 144.9, 128.4, 127.6, 126.9, 61.2, 56.4, 56.2, 42.9, 25.6, 23.2, 22.7, 15.4; HRMS for $C_{14}H_{22}NO$ [M+H]$^+$: m/z calcd 220.1696, found 220.1692.

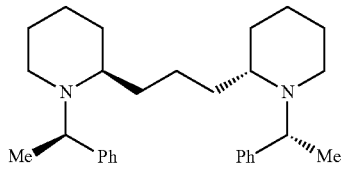

2v 1,3-bis((S)-1-((R)-1-Phenylethyl)piperidin-2-yl)propane (2v, unknown compound)

$^1$H NMR (CDCl$_3$, 400 MHz) δ (ppm): 7.41 (d, J=11.2 Hz, 4H), 7.29 (t, J=11.2 Hz, 4H), 7.23-7.15 (m, 2H), 4.00 (q, J=10.8 Hz, 2H), 2.73-2.70 (m, 18H), 2.41-2.33 (m, 2H), 2.25-2.15 (m, 2H), 1.65-1.30 (m, 2H), 1.24 (d, J=10.8 Hz, 6H); $^{13}$C NMR (CDCl$_3$, 100 MHz) δ (ppm): 146.3, 128.1, 127.6, 126.6, 57.0, 56.1, 45.1, 29.7, 29.4, 25.9, 22.8, 22.0, 14.8; HRMS for $C_{19}H_{43}N_2$ [M+H]$^+$: m/z calcd 419.3421, found 419.3419.

Discussion

Under the optimised conditions, the reaction proceeds smoothly with N-ethylpyridium salts bearing a variety of 2-aryl and alkyl substituents, affording the corresponding N-(1-phenylethyl)piperidines in good yields and almost uniformly high diastereoselectivities (>49:1) (see Table 1 above).

In contrast to heterogeneous catalytic methods, the reduction of the pyridinium ring occurred selectively in the presence of other potentially reducible functional groups, including, aryl bromides, esters and cyano, nitro and carbonyl groups (Table 1, Examples 7-10 and 20).

Heterocyclic substituents, such as pyridine, thiophene and furan, were also well tolerated albeit in diminished yields (Table 1, Examples 12-14).

The presence of other groups including protected amines and free alcohols did not inhibit the reaction (Table 1, Examples 19 and 21).

It is worth to note that 2,3-disubstituted piperidines could be obtained in excellent d.r. and moderate yield (Table 1, Example 23). Thus, this method allows for a broad range of chiral piperidines to be accessed with excellent diastereoselectivities in a single step from simple precursors.

In some cases, naturally occurring alkaloids such as coniine, previously always by multistep synthesis starting from complex materials, could be directly obtained by a simple debenzylation (Table 1, Example 17). Chiral bis-piperidines could also be produced by this method (Table 1, Example 22), which may find use in asymmetric catalysis as chiral diamine ligands.

Examples 25-37

Compounds prepared from other amines are shown in Table 2:

TABLE 2

Transamination of 2-phenylpyridiniums with various primary amines.[a]

| Example | Amine | Product | Yield [%][b] |
|---|---|---|---|
| 25 | (R)-1-phenylethylamine (Me, NH₂, Ph) | 3a | 78 |

TABLE 2-continued
Transamination of 2-phenylpyridiniums with various primary amines.[a]
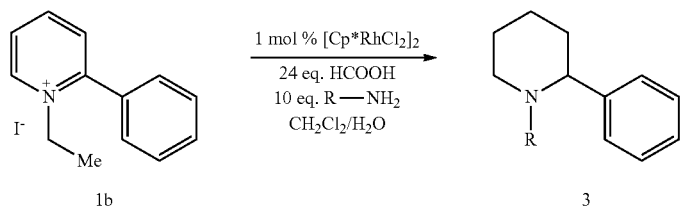
| Example | Amine | Product | Yield [%][b] |
|---------|-------|---------|--------------|
| 26 | (S)-1-cyclohexylethylamine | 3b | 88 |
| 27 | (R)-3,3-dimethyl-2-butylamine | 3c | 77 |
| 28 | cycloheptylamine | 3d | 77 |
| 29 | cyclohexylamine | 3e | 88 |

TABLE 2-continued
Transamination of 2-phenylpyridiniums with various primary amines.[a]
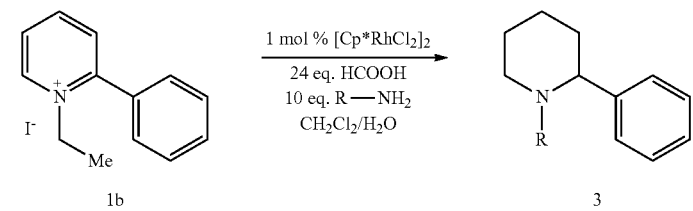
| Example | Amine | Product | Yield [%][b] |
|---|---|---|---|
| 30 | cyclopentyl-NH₂ | 3f (N-cyclopentyl-2-phenylpiperidine) | 64 |
| 31 | cyclobutyl-NH₂ | 3g (N-cyclobutyl-2-phenylpiperidine) | 72 |
| 32 | cyclopropyl-NH₂ | 3h (N-cyclopropyl-2-phenylpiperidine) | 64 |
| 33 | benzyl-NH₂ | 3i (N-benzyl-2-phenylpiperidine) | 83 |

TABLE 2-continued
Transamination of 2-phenylpyridiniums with various primary amines.[a]
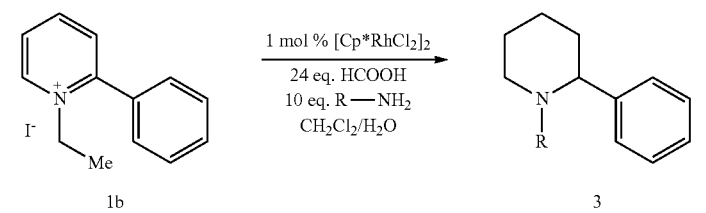
| Example | Amine | Product | Yield [%][b] |
|---|---|---|---|
| 34 | 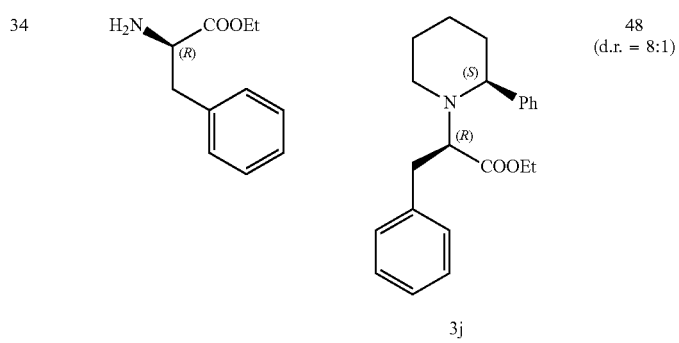 | | 48 (d.r. = 8:1) |
| 35 | 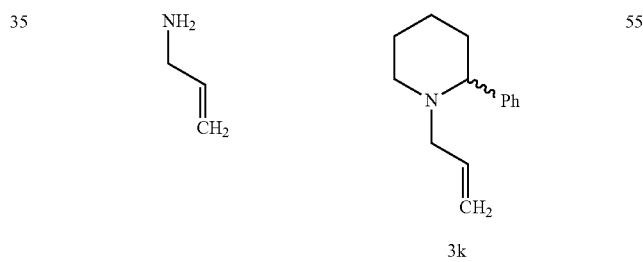 | | 55 |
| 36 | 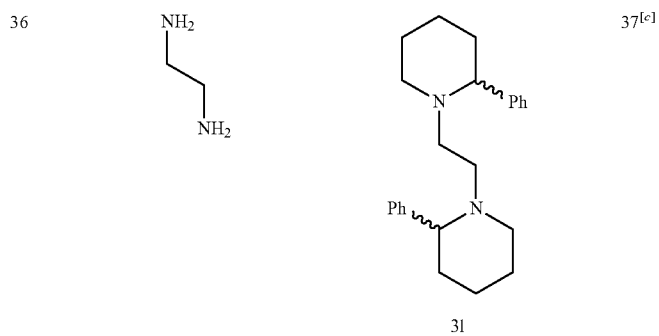 | | 37[c] |

TABLE 2-continued

Transamination of 2-phenylpyridiniums with various primary amines.[a]

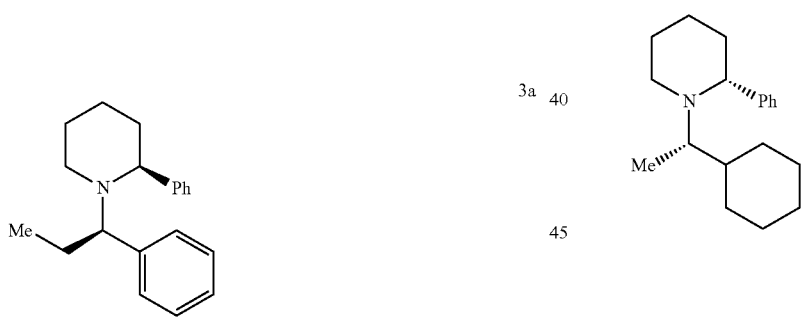

| Example | Amine | Product | Yield [%][b] |
|---|---|---|---|
| 37 | (4-amino-1-Boc-piperidine) | 3m | 68[d] |

[a]Reactions were carried out under the standard conditions given in Table 2 except for using different amines.
[b]Isolated yield.
[c]5.0 equivalent of amines were used.
[d]Reaction conditions: 1b (0.5 mmol), HCOOH (6.0 mmol), 1-Boc-4-aminopiperidine (0.5 mmol), Et$_3$N (2.0 mmol), [Cp*RhCl$_2$]$_2$ (5 μmol) and CH$_2$Cl$_2$/H$_2$O (3.75/0.25 mL), 40° C., 22 h.

Analytical Data of Sample Products:

(S)-2-Phenyl-1-((R)-1-phenylpropyl)piperidine (3a, unknown compound)

$^1$H NMR (CDCl$_3$, 400 MHz) δ (ppm): 7.54 (d, J=7.6 Hz, 2H), 7.43 (t, J=7.6 Hz, 2H), 7.36-7.29 (m, 5H), 7.25 (t, J=6.4 Hz, 1H), 3.62 (d, J=10.4 Hz, 1H), 3.51 (dd, J=9.6, 3.4 Hz, 1H), 2.78 (d, J=11.6 Hz, 1H), 2.32 (t, J=11.2 Hz, 1H), 1.93-1.30 (m, 8H), 0.68 (t, J=7.2 Hz, 3H); $^{13}$C NMR (CDCl$_3$, 100 MHz) δ (ppm): 145.3, 142.2, 128.9, 128.6, 128.0, 127.8, 127.1, 126.4, 65.8, 63.1, 45.5, 36.7, 26.4, 25.6, 15.3, 12.1; HRMS for C$_{20}$H$_{26}$N [M+H]$^+$: m/z calcd 280.2060, found 280.2060.

(R)-1-((S)-1-Cyclohexylethyl)-2-phenyl piperidine (3b, unknown compound)

$^1$H NMR (CDCl$_3$, 400 MHz) δ (ppm): 7.30-7.16 (m, 5H), 3.32 (dd, J=10.8, 2.8 Hz, 1H), 2.78 (d, J=11.6 Hz, 1H), 2.25-2.09 (m, 3H), 1.76-1.49 (m, 9H), 1.35-1.00 (m, 5H), 0.73 (d, J=6.4 Hz, 3H), 0.69-0.62 (m, 1H), 0.58-0.48 (m, 1H); $^{13}$C NMR (CDCl$_3$, 100 MHz) δ (ppm): 145.7, 128.2, 128.1, 126.6, 65.7, 57.5, 44.9, 41.1, 37.6, 31.2, 30.6, 26.9, 26.8, 26.6, 25.8, 8.4; HRMS for C$_{19}$H$_{30}$N [M+H]$^+$: m/z calcd 272.2373, found 272.2378.

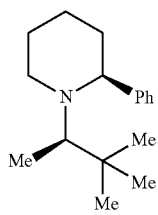

(S)-1-((R)-3,3-Dimethylbutan-2-yl)-2-phenylpiperidine (3c, unknown compound)

$^1$H NMR (CDCl$_3$, 400 MHz) δ (ppm): 7.23-7.10 (m, 5H), 3.19-3.16 (m, 1H), 2.89 (d, J=11.2 Hz, 1H), 2.20-2.11 (m, 2H), 1.69-1.47 (m, 5H), 1.27-1.16 (m, 1H), 0.73-0.71 (m, 12H); $^{13}$C NMR (CDCl$_3$, 100 MHz) δ (ppm): 145.8, 128.5, 128.1, 126.8, 67.3, 60.2, 48.4, 37.2, 35.2, 28.9, 26.6, 25.9, 5.6; HRMS for C$_{17}$H$_{28}$N [M+H]$^+$: m/z calcd 246.2216, found 246.2209.

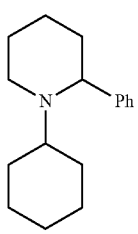

1-Cyclohexyl-2-phenylpiperidine (3e, unknown compound)

$^1$H NMR (CDCl$_3$, 400 MHz) δ (ppm): 7.32-7.19 (m, 5H), 3.41 (dd, J=10.8, 2.8 Hz, 1H), 3.02 (d, J=11.2 Hz, 1H), 2.32-2.25 (m, 2H), 1.77-1.25 (m, 12H), 1.14-0.73 (m, 4H); $^{13}$C NMR (CDCl$_3$, 100 MHz) δ (ppm): 145.6, 128.4, 127.5, 126.7, 65.7, 58.2, 46.4, 37.3, 31.8, 26.72, 26.68, 26.64, 26.0, 25.6, 23.8; HRMS for C$_{17}$H$_{26}$N [M+H]$^+$: m/z calcd 244.2060, found 244.2063.

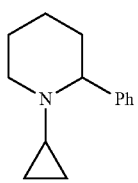

1-Cyclopropyl-2-phenylpiperidine (3h, unknown compound)

$^1$H NMR (CDCl$_3$, 400 MHz) δ (ppm): 7.31-7.21 (m, 5H), 3.17 (d, J=11.6 Hz, 1H), 3.09 (dd, J=10.4, 3.2 Hz, 1H), 2.25 (td, J=11.8, 3.0 Hz, 1H), 1.85-1.51 (m, 5H), 1.45-1.26 (m, 2H), 0.28-0.13 (m, 2H), −0.01-0.26 (m, 2H); $^{13}$C NMR (CDCl$_3$, 100 MHz) δ (ppm): 144.4, 128.7, 127.9, 127.0, 71.3, 56.1, 39.1, 34.6, 26.1, 24.9, 9.6, 4.0; HRMS for C$_{14}$H$_{20}$N [M+H]$^+$: m/z calcd 202.1590, found 202.1595.

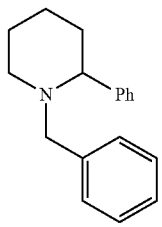

1-Benzyl-2-phenylpiperidine (3i)

$^1$H NMR (CDCl$_3$, 400 MHz) δ (ppm): 7.46 (d, J=7.2 Hz, 2H), 7.31 (t, J=7.8 Hz, 2H), 7.28 (d, J=4.4 Hz, 4H), 7.25-7.18 (m, 2H), 3.76 (d, J=13.6 Hz, 1H), 3.11 (dd, J=11.0, 2.6 Hz, 1H), 2.96 (d, J=11.6 Hz, 1H), 2.81 (d, J=13.2 Hz, 1H), 1.98-1.89 (m, 1H), 1.81-1.74 (m, 2H), 1.67-1.53 (m, 3H), 1.42-1.31 (m, 1H); $^{13}$C NMR (CDCl$_3$, 100 MHz) δ (ppm): 145.9, 140.0, 128.8, 128.6, 128.1, 127.6, 127.0, 126.6, 69.3, 59.9, 53.5, 37.2, 26.1, 25.4; HRMS for C$_{18}$H$_{22}$N [M+H]$^+$: m/z calcd 252.1752, found 252.1748.

Discussion:

Although the in situ incorporation of a PEA auxiliary and subsequent reduction to give chiral piperidines is the most immediate use of this transamination-reduction reaction, it can also be used to furnish the alkylation of piperidines, starting from pyridinium precursors, using amines as the alkylating agent, as shown in Table 2. This offers an advantage in cases where an effective alkylating agent is not available due to its instability or lack of reactivity. For instance, N-cyclopropylpiperidine 3h, which is not obtainable by alkylation or reductive amination, was obtained in a yield of 64% using cheap reagents. In addition, due to the retention of the nitrogen atom in the reactant amine, the stereochemistry of this unit is completely conserved. Using this method, a variety of N-alkyl piperidines 3a-m bearing cyclic and acyclic alkyl groups were synthesised in a single step, including those bearing optically active N-alkyl groups 3a-c, 3j (Table 2, Examples 24-26 and 33).

Example 41—Preparation of $^{15}$N-Labled-Benzyl Coniine

The nitrogen atom in the product was shown to be derived from the added amine, and not the parent pyridinium salt by the use of $^{15}$N labelled benzylamine. Subsequent deprotection, e.g. de-benzylation by hydrogenolysis, allows for a convenient, traceless, method for the $^{15}$N labelling of piperidine derivatives.

The effectiveness of this method was demonstrated in a one-pot, two-step synthesis of a $^{15}$N labelled alkaloid, a coniine derivative, directly from a neutral pyridine

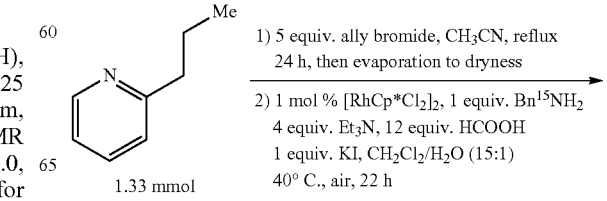

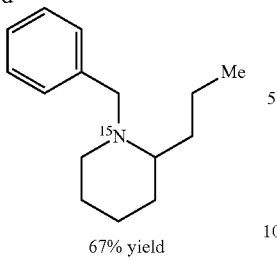

67% yield

REFERENCES 1. (a) D. O'Hagan, *Nat. Prod. Rep.* 2000, 17, 435; (b) S. Laschat, T. Dickner, *Synthesis* 2000, 1781; (c) P. M. Weintraub, J. S. Sabol, J. M. Kane, D. R. Borcherding, *Tetrahedron* 2003, 59, 2953; (d) M. G. P. Buffat, *Tetrahedron* 2004, 60, 1701; (e) P. Merino, T. Tejero, G. Greco, E. Marca, I. Delso, A. Gomez-SanJuan, R. Matute, *Heterocycles* 2012, 84, 75.
2. (a) F. Glorius, *Org. Biomol. Chem.* 2005, 3, 4171; (b) D. S. Wang, Q. A. Chen, S. M. Lu, Y. G. Zhou, *Chem. Rev.* 2012, 112, 2557; (c) Z. Yu, W. Jin, Q. Jiang, *Angew. Chem. Int. Ed.* 2012, 51, 6060.

The invention claimed is:

1. A process for the preparation of a substituted piperidine compound of formula I:

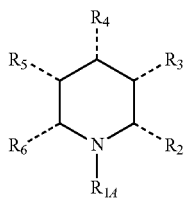

wherein:

$R_{1A}$ has the formula X shown below:

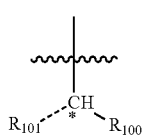

wherein

~~~ represents the point of attachment to the N atom of the piperidine ring,

* represents a chiral carbon atom; and $R_{100}$ and $R_{101}$ are different substituent groups that, together with the carbon atom to which they are attached, form a substituent group selected from (1-10C)alkyl, (2-10C)alkenyl, (2-10C)alkynyl, (3-12C)cycloalkyl, (3-12C)cycloalkyl(1-6C)alkyl, (3-12C)cycloalkenyl, (3-12C)cycloalkenyl(1-6C)alkyl, aryl, aryl(1-6C)alkyl, heteroaryl, heteroaryl(1-6C)alkyl, heterocyclyl, heterocyclyl(1-6C)alkyl, each of which is optionally further substituted by one or more groups $Q_1$;

$R_2$, $R_3$, $R_4$, $R_5$, and $R_6$ are each independently selected from hydrogen or a substituent group selected from (1-10C)alkyl, (2-10C)alkenyl, (2-10C)alkynyl, (3-12C)cycloalkyl, (3-12C)cycloalkyl(1-6C)alkyl, (3-12C)cycloalkenyl, (3-12C)cycloalkenyl(1-6C)alkyl, aryl, aryl(1-6C)alkyl, heteroaryl, heteroaryl(1-6C)alkyl, heterocyclyl, heterocyclyl(1-6C)alkyl, each of which is optionally further substituted by one or more groups, with the proviso that at least one of $R_2$, $R_3$, $R_4$, $R_5$, and $R_6$ is a substituent group;

and wherein $Q_1$ is selected from halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $Q_1$ is a group of the formula:

$-L^1-L^2-R_A$ wherein $L^1$ is absent or a linker group of the formula $-[CR_b R_c]_n-$ in which n is an integer selected from 1, 2, 3 or 4, and $R_b$ and $R_c$ are each independently selected from hydrogen or (1-4C)alkyl;

$L^2$ is absent or is selected from O, S, SO, $SO_2$, $N(R_d)$, C(O), C(O)O, OC(O), $CH(OR_d)$, $C(O)N(R_d)$, $N(R_d)C(O)$, $N(R_d)C(O)N(R_e)$, $S(O)_2N(R_d)$, or $N(R_d)SO_2$, wherein $R_d$ and $R_e$ are each independently selected from hydrogen or (1-4C)alkyl; and $R_A$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_A$ is optionally further substituted by one or more substituent groups independently selected from oxo, halo, cyano, nitro, hydroxy, $NR_fR_g$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_fR_g$, and $SO_2NR_fR_g$; wherein $R_f$ and $R_g$ are each independently selected from hydrogen, (1-4C)alkyl or (3-6C)cycloalkyl or (3-6C)cycloalkyl(1-2C)alkyl; or $R_f$ and $R_g$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_hR_i$ (where $R_h$ and $R_i$ are each independently selected from hydrogen, (1-3C)alkyl, (3-6C)cycloalkyl, or (3-6C)cycloalkyl(1-2C)alkyl);

or $R_A$ is a group having the formula:

$-L^3-L^4-R_B$ wherein $L^3$ is absent or a linker group of the formula $-[CR_j R_k]_n-$ in which n is an integer selected from 1, 2, 3 or 4, and $R_j$ and $R_k$ are each independently selected from hydrogen or (1-4C)alkyl;

$L^4$ is absent or is selected from O, S, SO, $SO_2$, $N(R_l)$, C(O), C(O)O, OC(O), $CH(OR_l)$, $C(O)N(R_l)$, $N(R_l)$ C(O), $N(R_l)C(O)N(R_m)$, $S(O)_2N(R_l)$, or $N(R_l)SO_2$, wherein $R_l$ and $R_m$ are each independently selected from hydrogen or (1-4C)alkyl; and $R_B$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl;

the process comprising reacting, in the presence of a suitable solvent, a pyridinium salt of the formula:

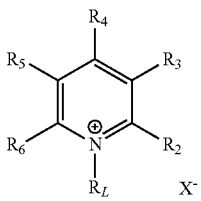

wherein:
$X^-$ is a counter ion,
$R_L$ is a substituent group selected from (1-10C)alkyl, (2-10C)alkenyl, (2-10C)alkynyl, (3-12C)cycloalkyl, (3-12C)cycloalkyl(1-6C)alkyl, (3-12C)cycloalkenyl(1-6C)alkyl, aryl(1-6C)alkyl, heteroaryl(1-6C)alkyl, or heterocyclyl(1-6C)alkyl, each of which is optionally further substituted by one or more groups $Q_1$ as defined above,
and $R_2$, $R_3$, $R_4$, $R_5$, and $R_6$ are as defined above;
with an amine of the formula:

$$H_2N-R_{14}$$

wherein:
$R_{14}$ is a substituent group as defined above and the nitrogen is $^{14}N$ or $^{15}N$;
in the presence of a hydrogen donor and a catalyst that is capable of generating hydride from the hydrogen donor.

2. The process according to claim 1, wherein one or more of $R_2$, $R_3$, $R_4$, $R_5$, and $R_6$ is a substituent group and the carbon atom of the piperidine ring to which the substituent group is attached is chiral and the group $R_{14}$ comprises a chiral carbon atom.

3. The process according to claim 1, wherein 1, 2 or 3 of the groups $R_2$, $R_3$, $R_4$, $R_5$ and $R_6$ are a substituent group and the remaining groups are hydrogen.

4. The process according to claim 3, wherein 1 or 2 of the groups $R_2$, $R_3$, $R_4$, $R_5$ and $R_6$ are a substituent group and the remaining groups are hydrogen.

5. The process according claim 1, wherein $X^-$ is bromo or iodo.

6. The process according to claim 1, wherein the amine is present in an amount of 1 and 20 molar equivalents of amine relative to the pyridinium ion are present.

7. The process according to claim 1, wherein the hydrogen donor is selected from hydrogen gas, formic acid or isopropanol.

8. The process according to claim 1, wherein the ratio of hydrogen donor to amine is between 1:1 and 10:1 (molar equivalents of hydrogen donor to amine).

9. The process according to claim 1, wherein the solvent comprises between 1 and 50% by volume of water as a co-solvent.

10. The process according to claim 1, wherein the catalyst is a metal complex that reacts with hydrogen gas or formic acid to form a metal hydride.

11. The process according to claim 1, wherein the catalyst has the formula $$[ArMX_2]_2$$

where Ar is pentamethylcyclopentadienyl or an arene, such as cymene; M is a transition metal (e.g. Rh, Ir and Ru); and X is a halide, such as chloro, bromo or iodo.

12. A process according to claim 11, wherein the arene is cymene.

13. A process according to claim 11, wherein the transition metal is selected from Rh, Ir, or Ru.

14. A process according to claim 11, wherein the halide is selected from chloro, bromo or iodo.

* * * * *

UNITED STATES PATENT AND TRADEMARK OFFICE
CERTIFICATE OF CORRECTION

PATENT NO. : 9,981,957 B2
APPLICATION NO. : 15/128829
DATED : May 29, 2018
INVENTOR(S) : Jianliang Xiao et al.

It is certified that error appears in the above-identified patent and that said Letters Patent is hereby corrected as shown below:

In the Claims

Column 45 Claim 1, Line 57, please insert -- * -- at the beginning of the line.

Signed and Sealed this
Twenty-first Day of August, 2018

Andrei Iancu
*Director of the United States Patent and Trademark Office*